United States Patent
Angelucci et al.

(12)

(10) Patent No.: US 6,376,617 B1
(45) Date of Patent: Apr. 23, 2002

(54) BIOACTIVE DERIVATIVES OF CAMPTOTHECIN

(75) Inventors: Francesco Angelucci, Milan; Gabriele Fachin, Pavia; Valeria Caiolfa; Antonino Suarato, both of Milan, all of (IT)

(73) Assignee: Pharmacia & Upjohn S.p.A., Milan (IT)

(*) Notice: Subject to any disclaimer, the term of this patent is extended or adjusted under 35 U.S.C. 154(b) by 0 days.

(21) Appl. No.: 09/308,667

(22) PCT Filed: Sep. 25, 1998

(86) PCT No.: PCT/EP98/06185

§ 371 Date: Jun. 3, 1999

§ 102(e) Date: Jun. 3, 1999

(87) PCT Pub. No.: WO99/17805

PCT Pub. Date: Apr. 15, 1997

(30) Foreign Application Priority Data

Oct. 3, 1997 (GB) ............................................. 9721070

(51) Int. Cl.$^7$ ...................... C08F 220/56; C08F 224/00; C07D 491/12; A61K 31/4355
(52) U.S. Cl. .................. 525/329.4; 546/48; 546/51; 546/53; 514/19; 514/283
(58) Field of Search ................................ 546/48, 51, 53; 514/19, 283; 525/329.4

(56) References Cited

U.S. PATENT DOCUMENTS

| 5,362,831 | A | | 11/1994 | Mongelli et al. |
| 5,473,055 | A | | 12/1995 | Mongelli et al. |
| 5,569,720 | A | | 10/1996 | Mongelli et al. |
| 5,571,785 | A | | 11/1996 | Angelucci et al. |
| 5,719,265 | A | | 2/1998 | Mongelli et al. |
| 5,773,522 | A | * | 6/1998 | Angelucci et al. ....... 525/329.4 |

* cited by examiner

Primary Examiner—Alan L. Rotman
Assistant Examiner—Rita Desai
(74) Attorney, Agent, or Firm—Oblon, Spivak, McClelland, Maier & Neustadt, P.C.

(57) ABSTRACT

Water soluble polymeric conjugates of camptothecin consist essentially of N-(2-hydroxypropyl)methacryloylamide units linked via a spacer group to a residue of a camptothecin such as irinotecan or its non-soluble metabolite, 7-ethyl-10-hydroxy-camptothecin. The conjugates possess enhance antitumor activity and decreased toxicity with respect to the free drug. A process for their preparation and the pharmaceutical compositions containing them are also described.

12 Claims, No Drawings

BIOACTIVE DERIVATIVES OF CAMPTOTHECIN

BACKGROUND OF THE INVENTION

Field of the Invention

The present invention provides water soluble polymeric conjugates of camptothecin possessing enhanced antitumor activity and decreased toxicity with respect to the free drug. 7-Ethyl-10-hydroxy-camptothecin (1a, Z=H), a topoisomerase I inhibitor belonging to the class of camptothecin, is a non-soluble compound and it is recognized as the active metabolite of irinotecan (CPT-11, 1b, Z=1,4'-bipiperidinecarbonyl, Cancer Res.: 50,1715–20, 1990).

(1)

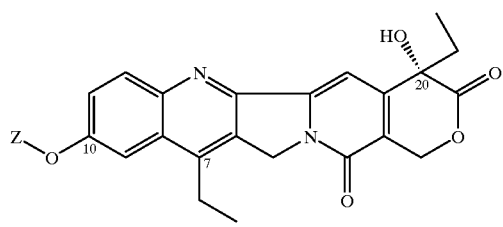

DETAILED DESCRIPTION OF THE PREFERRED EMBODIMENTS

The invention provides a polymeric conjugate which is denoted herein a (A) and which consists essentially of:
(i) from 85 to 97 mol % of N-(2-hydroxypropyl) methacryloylamide units represented by formula (2)

(2)

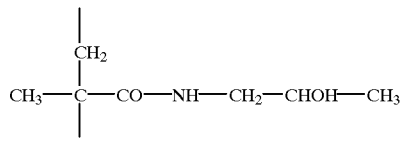

(ii) from 3 to 15 mol % of units represented by formula (3)

(3)

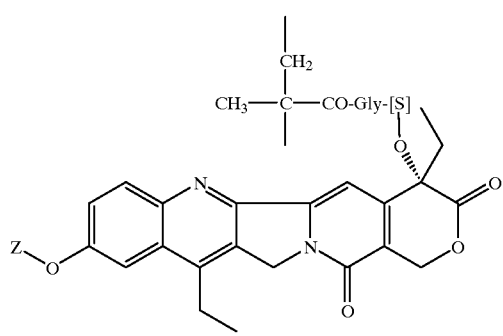

wherein [S] is a spacer group; Z is hydrogen, $R_1CO$ in which $R_1$ is $C_1$-$C_6$ alkyl or the group 1,4'-bipiperidine and (iii) from 0 to 12 mol % of -methacryloyl-glycine or N-(2-hydroxypropyl)methacryloyl-glycinamide units represented by formula (4)

(4)

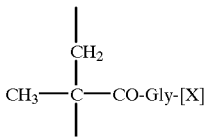

wherein [X] represents hydroxy or a residue of formula —NH—$CH_2$—CH(OH)—$CH_3$.

The polymer of the present invention may also be represented as follows:

$[(2)]_x$; $[(3)]_y$; $[(4)]_z$ wherein (2), (3) and (4) are units of the formula as above defined, and x is from 85 to 97 mol %, y is from 3 to 15 mol % and z is from 0 to 12 mol %. Preferably, the polymeric conjugate (A) contains the N-(2-hydroxypropyl) methacryloyl amide units represented by the formula (2) in a proportion of 90% or more; more preferably 90%. The conjugate may also contain from 3 to 10 mol % of the 20-O-(methacryloyl-glycyl-peptidyl)camptothecin units represented by the formula (3), more preferably 10 mol % of such units. Preferably A does not contain residues of formula (4), i.e. z is 0.

The spacer group is susceptible to intratumoral enzymatic hydrolysis. The spacer group may be an amino acid residue or a peptide spacer, for example from 2 to 4 amino acid residues long. Preferably the spacer group [S] is selected from Ala-Gly, Phe-Gly, Leu-Gly, Phe-Ala, Leu-Leu, Phe-Leu-Gly, Leu-Leu-Gly and Phe-Leu-Gly-Gly.

Preferably, the polymeric conjugate (A) contains the units represented by formula (3) wherein Z is H.

Content of active camptothecin derivative of formula (1) in the conjugate of formula A may be from 2 to 15% (weight/weight), more preferably 10% (w/w).

The invention also provides a process for preparing a polymeric conjugate as defined above, which process comprises reacting a camptothecin derivative of formula (5):

(5)

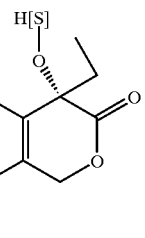

wherein [S] and Z are as defined above, with a polymer (B) consisting essentially of:
(i) from 85 to 97 mol % of N-(2-hydroxypropyl) methacryloylamide units represented by formula (2)

(2)

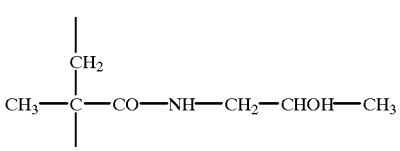

(iv) from 3 to 15 mol % of N-methacryloyl-glycyl units represented by formula (6)

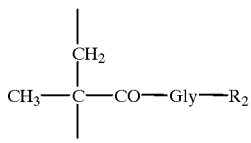

(6)

wherein $R_2$ is:
the residue of an active ester, or
hydroxy;
and optionally displacing the remaining active ester groups with 1-amino-2-propanol.

The invention also provides 20-O-peptidyl-camptothecin derivatives of formula (5')

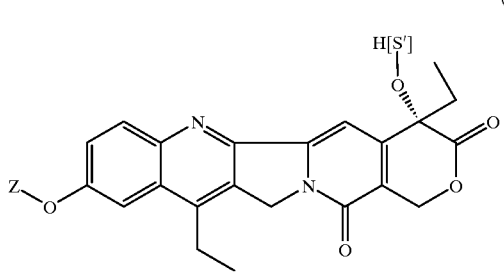

(5')

wherein the group [S'] is a peptide spacer, for example from 2 to 4 amino acid residues long, preferably selected from Ala-Gly, Phe-Gly, Leu-Gly, Phe-Ala, Leu-Leu, Phe-Leu-Gly, Leu-Leu-Gly and Phe-Leu-Gly-Gly; Z is as defined above, and their salt derivatives. Such compounds are prepared by condensing camptothecin derivatives of formula 1 as above defined with a N-protected-peptidyl derivative of formula (7):

(7)

wherein [S'] is as defined above and $R_3$ represents an amino-protecting group, such as Boc, FMOC, triphenylsilyl, diphenylmethylene or triphenylmethyl, and P is a residue of an activated ester, such as p-nitrophenoxy or N-hydroxysuccinimido, to give a compound represented by formula (8):

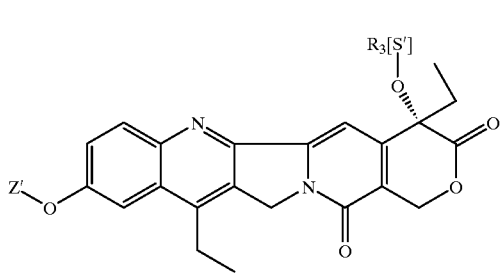

(8)

wherein Z' is $R_3$[S'] or $R_1$CO, wherein $R_1$, $R_3$ and [S'] are as defined above and then deblocking the N-protecting group of the substituent at position C-20 from the resulting compound. The compounds of formula (5) as defined above may be analogously prepared.

Preparation of compounds of formula (7) follows standard synthetic procedures that are known from the literature. Suitable N-protected-peptidyl derivatives of formula 7 include, for example, N-(tri-phenylmethyl)-L-phenylalanyl-L-leucyl-glycyl p-nitrophenylester (7a), N-(t-Butoxycarbonyl)-L-phenyl-alanyl-L-leucyl-glycyl p-nitrophenylester (7b). Thus, for example, 7-ethyl-10-hydroxy-camptothecin (1a) may be allowed to react with a molar excess, for example up to five-fold molar excess or more, especially 2 mol.equivalent, of a N-protected-peptidyl derivative of formula (7) in anhydrous solvent such as dry dimethylformamide in the presence of 4-dimethylaminopyridine. In this manner, the protected amino acid is introduced at both hydroxylated positions 10-OH and 20-O of compound 1a to give compound of formula (8a: Z=$R_3$ [S']).

The reaction can typically be effected for from 8 to 48 hours. The reaction is typically carried out at a temperature from 15 to 40° C. The substituent group at position 10-OH and the amino-protected group $R_3$ of the substituent at 20-OH are removed by an appropriate deprotecting agent to give the 7-ethyl-10-hydroxy-20-O-peptidylcamptothecin derivative of formula (5a: Z=H). Deprotection may be therefore achieved by acid treatment, such as treatment with acetic acid, a mixture of acetic acid and 1.5N aqueous hydrochloric acid or 90% aqueous trifluoroacetic acid from one to 6 hours at temperature from 10 to 30° C.; preferably for two hours at room temperature.

The condensation of derivative of formula (5) with the polymer of formula (B), is carried out in conditions capable of preserving the nature of linkage between 7-ethyl-10-(substituted)-camptothecin and spacer [S] as well as that of the conjugate.

Polymers consisting essentially of from 85 to 97 mol % of N-(2-hydroxypropyl)methacryloylamide units of formula (2) and from 15 to 3 mol % of N-methacryloyl-glycine units of formula (6), are prepared by copolymerization of N-(2-hydroxypropyl)methacrylamide with N-methacryloyl-glycine or methacryloyl-glycine active-ester derivatives, as described in Makromol.Chem. 178, 2159 (1977). $R_2$ may represent a phenoxy group which is substituted on the phenyl ring by one or more electron-withdrawing groups, such as nitro or halogen. Preferably $R_2$ represent p-nitrophenoxy. Preferably, the reaction between a polymer in which $R_2$ represents the residue of active ester and a compound of formula (5) to prepare the polymeric conjugate of the invention is carried out in an anhydrous polar organic solvent such as dimethylsulfoxide. The reaction can typically carried out at temperature from 15 to 30° C., preferably at room temperature for 15 hours; then the aminolysis of the remaining active ester groups can be performed in the presence of 1-amino-2-propanol at room temperature, from 0.5 to 1 hour. The conjugate suitably is precipitate with ethyl acetate, dissolved in ethanol and reprecipitated with ethyl acetate.

For example, the polymer in which $R_2$ represents the residue of an active ester, provided at a concentration of 15% (w/v) in dry dimethylsulfoxide, is treated with 7-ethyl-10-hydroxy-20-O-peptidyl-camptothecin derivative of formula (5a), 3% (w/v), at room temperature for 15 hours. Then 1-amino-2-propanol, 0.1% (w/v) is added and the reaction mixture is kept at room temperature for 1 hour. The conjugate can be precipitated with ethyl acetate, collected, washed with ethyl acetate, then dissolved with absolute ethanol at a concentration of 10% (w/v) and precipitated again with ethyl acetate to give the conjugate of formula (A) according to the invention.

The content of active drug (1), in polymeric conjugate of the invention is determined by HPLC or absorbance spectroscopy analysis.

The polymer-bound derivatives of formula (A) are in the range of 5.000 to 45.000 molecular weight, preferably from 18.000 to 35.000. Polymeric drug derivatives of formula (A) are water soluble and show enhanced antitumor activity and reduced toxicity in comparison with the free 7-ethyl-10-hydroxy-camptothecin. They are useful in the treatment of leukemia and solid tumors, such as colon, colo-rectal, ovarian, mammary, prostate, lung, kidney and also melanoma tumors. A human can therefore be treated by a method comprising administering thereto a therapeutically effective amount of a polymeric conjugate of the invention. The condition of the human patient can thus be improved.

The dosage range adopted will depend on the route of administration and on the age, weight and condition of the patient being treated. The polymeric conjugates of formula (A) as well as soluble salt derivatives of formula (5') are typically administered by parenteral route, for example intramuscularly, intravenously or by bolus infusion. A suitable dose range is from 1 to 1000 mg of equivalent per $m^2$ body surface area of active drug of formula (1), for instance from 10 to 100 $mg/m^2$ The polymeric conjugate (A) or soluble salt derivatives of formula (5') may be formulated into a pharmaceutical composition together with a pharmaceutically carrier or diluent. Typically they are formulated for parenteral administration, for example by dissolution in water for injection or physiological saline.

The following Examples illustrate the invention.

EXAMPLE 1

Preparation of: 7-ethyl-10-hydroxy-20-O-(L-phenylalanyl-L-leucyl-glycyl)camptothecin (5c; H[S]=H-Phe-Leu-Gly-, Z=H)

7-ethyl-10-hydroxy-camptothecin (1a 0.8 g, 2 mmol), N-(tert-Butoxycarbonyl)-L-phenyl-alanyl-L-leucyl-glycyl p-nitrophenylester (7b; 3.3 g, 6 mmol) and 4-dimethylaminopyridine (0.5 g, 4 mmol) were dissolved with dry dimethylsulfoxide (30 ml) and kept at room temperature for three days under stirring. After that the reaction mixture was poured in 0.1N aqueous hydrochloric acid (500 ml) to give a precipitate which was collected on a sintered glass funnel. The solid material was dissolved in ethyl acetate (200 ml) and washed with saturated aqueous solution of sodium hydrogen carbonate (2×100 ml) and water (2×100 ml). The organic phase was separated, dried over anhydrous sodium sulfate and evaporated under reduced pressure. The residue was treated with 90% aqueous trifluoroacetic acid (40 ml) for three hours, then the solvent was removed under reduced pressure. The crude material was dissolved in methanol (50 ml), diluted with methylene chloride (200 ml), washed with saturated solution of sodium hydrogen carbonate (3×100 ml) and water (3×100 ml). The organic phase was dried over anhydrous sodium sulfate evaporated under reduced pressure and flash chromatographed on silica gel using a mixture of methylene chloride/methanol (95/5 v/v) as eluting system to give 0.93 g of the title compound (5c).

TLC on Kieselgel plate $F_{254}$ (Merck), eluting system methylene chloride/methanol (95/5 v/v), $R_f$=0.18.

$^1$H-NMR (200 MHz, DMSO) 0.80 (d, J=5.7 Hz, 6H, δ+δ'-Leu); 0.90 (t, J=7.3 Hz, 3H, CH$_3$—CH$_2$-20); 1.26 (t, J=7.6 Hz, 3H, CH$_3$—CH$_2$-7); 1.45 (m, 3H, β+β'+γ-Leu); 2.11 (q, J=7.3 Hz, 2H, CH$_3$—CH$_2$-20); 2.56 (dd, J=13.2, 8.2 Hz, 1H, β-Phe); 2.88 (dd, J=13.2, 4.4 Hz, 1H, β'-Phe); 3.05 (q, J=7.6 Hz, 2H, CH$_3$—CH$_2$-7); 3.37 (dd, J=8.2, 4.4 Hz, 1H, α-Phe); 3.99 (dd, J=18.0, 5.7 Hz, 1H, α-Gly); 4.14 (dd, J=18.0, 5.7 Hz, 1H, α'-Gly); 4.35 (m, 1H, α-Leu); 5.24 (s, 2H, CH$_2$-5); 5.47 (s, 2H, CH$_2$-17); 7.02 (s, 1H, H-14); 7.05–7.45 (m, 7H, H-9+H-11+Ar-Phe); 7.93 (d, J=8.6 Hz, 1H, NH-Leu); 7.99 (d, J=9.8 Hz, 1H, H-12); 8.45 (t, J=5.7 Hz, 1H, NH-Gly).

EXAMPLE 2

Preparation of: 7-ethyl-10-hydroxy -20-O-(L-phenylalanyl-L-leucyl-glycyl)camptothecin hydrochloride (5d; H[S]=H-Phe-Leu-Gly-, Z=H)

7-ethyl-10-hydroxy-20-O-(L-phenylalanyl-L-leucyl-glycyl)camptothecin (5c, 0.5 g), prepared as described in Example 1, was dissolved in methylene chloride (10 ml), cooled at 0° C. and treated with a 1N methanolic solution of anhydrous hydrochloric (0.2 ml). After one minute, ethyl ether (100 ml) was added to the solution. The precipitate was collected, washed with ethylene chloride and dried to give 0.5 g of the title compound (5d).

EXAMPLE 3

Preparation of: copolymer of N-(2-hydroxypropyl) methacrylamide, {7-ethyl-10-hydroxy-20-O-[N-methacryloyl-glycyl-L-phenylalanyl-L-leucyl-glycyl]camptothecin} and N-(2-hydroxypropyl) methacryloylglycinamide (A1)

Polymeric precursor (B1) ($R_2$=p-nitrophenyloxy, 2.58 g, containing 1.16×10$^{-3}$ eq. of p-nitro phenyl), prepared as described in Makromol.Chem. 178, 2159 (1977), was dissolved with DMSO dry (15 ml) and added with 7-ethyl-10-hydroxy-20-O-(L-phenylalanyl-L-leucyl glycyl) camptothecin (5c; 0.71 g, 1 mmol). The reaction mixture was kept at room temperature for 22 hours under stirring, then 2-propanolamine (0.05 ml) was added and the mixture left under stirring for one more hour. After that, the reaction mixture was precipitated with ethyl acetate (200 ml) and left under stirring for 30 min. The solid material was collected on a sintered glass funnel, washed with ethyl acetate (200 ml) and ethyl ether (100 ml) and then dissolved with ethanol (30 ml). The alcoholic solution was treated with wet DOWEX-50, sulphonic form, (1.2 g) under stirring for 30 min. and, after that, was added dropwise to n-hexane (200 ml). The precipitate was collected on a sintered glass funnel, washed with ethyl ether and dried to constant weight to give 2.8 g of the title compound (A1).

Weight-average molecular weight (Mw): 24.300.

Polydispersity (Mw/Mn): 1.63.

Content of 7-ethy-10-hydroxy-camptothecin, determined after alkaline hydrolysis, 10% w/w.

Antitumor Activity

Campound A1 was tested on human colon carcinoma (HT29) transplanted in nude mice, in comparison with the free drug 7-ethyl-10-hydroxycamptothecin (1a) by i.v. route. A1 was found non toxic at all tested doses and gave 98% tumor inhibition at the highest tested dose of 20 mg/kg (Table 1).

TABLE 1

Antitumor Activity of A1 on human colon carcinoma (HT29) in comparison with 7-ethyl-10-hydroxycamptothecin (1a).

| compound | treatment schedule | Dose mg/kg | Total Dose mg/kg | TI% 46$^{th}$ day | Tox |
|---|---|---|---|---|---|
| A1 | iv q4dx8 | 5 | 40 | 77 | 0/7 |
|  |  | 10 | 80 | 91 | 0/7 |
|  |  | 20 | 160 | 98 | 0/7 |
| 1a Reference | iv q4dx6 | 20 | 120 | 97 | 1/7 |

Tumor fragment were implanted sc. Treatment started when tumor was palpable. TI % (tumor inhibition %) was calculated at day 46.

What is claimed is:

1. A polymeric conjugate, which consists essentially of:

(1) from 85 to 97 mol % of N-(3-hydroxypropyl) methacryloylamide units represented by the formula (2):

(2)

$$CH_3-\underset{\underset{CH_2}{|}}{C}-CO-NH-CH_2-CHOH-CH_3$$

(ii) from 3 to 15 mol % of units represented by the formula (3):

(3)

[structure: methacryloyl-Gly-(S)-O-camptothecin derivative with Z—O substituent]

wherein (S) is a spacer group; Z is hydrogen, $R_1CO$ in which $R_1$ is $C_1$–$C_6$ alkyl or the group 1,4'-bipiperidine; and (iii) from 0 to 12 mol % of N-methacryloyl-glycine or N-(2-hydroxypropyl)methacryloyl-glycinamide units represented by the formula (4):

(4)

$$CH_3-\underset{\underset{CH_2}{|}}{C}-CO-Gly-(X)$$

wherein (X) represents hydroxy or a group of the formula —NH—CH$_2$CH(OH)—CH$_3$.

2. The polymeric conjugate according to claim 1, which contains the N-(2-hydroxypropyl)methacryloylamide units represented by the formula (2) in a molar proportion of 90%.

3. The polymeric conjugate according to claim 1, which contains 10 mol % of the 20-O-(methacryloyl-glycyl-peptidyl)camptothecin units represented by the formula (3).

4. The polymeric conjugate according to claim 1, wherein the spacer group (S) in the units of the formula (3) is selected from Ala-Gly, Phe-Gly, Leu-Gly, Phe-Ala, Leu-Leu, Phe-Leu-Gly, Leu-Leu-Gly and Phe-Leu-Gly-Gly.

5. The polymeric conjugate according to claim 1, wherein Z in the units of the formula (3) is H.

6. The polymeric conjugate according to claim 1, in which the content of the active camptothecin of the formula (1):

(1)

[camptothecin structure with HO and Z—O substituents]

wherein Z is as defined in claim 1, is 10% (w/w).

7. A process for preparing a polymeric conjugate as defined in claim 1, which process comprising reacting a camptothecin compound of the formula (5):

(5)

[camptothecin structure with H[S]—O and Z—O substituents]

wherein (S) and Z are as defined in claim 1, with a polymer consisting essentially of (i) from 85 to 97 mol % of N-(2-hydroxypropyl) methacryloylamide units represented by the formula (2):

(2)

$$CH_3-\underset{\underset{CH_2}{|}}{C}-CO-NH-CH_2-CHOH-CH_3$$

(iv) from 3 to 15 mol % of N-methacryloyl-glycyl units represented by the formula (6):

(6)

$$CH_3-\underset{\underset{CH_2}{|}}{C}-CO-Gly-R_2$$

wherein $R_2$ is:
the residue of an active ester, or
hydroxy;

and optionally displacing the remaining active ester groups with 1-amino-2-propanol.

8. A 20-O-peptidyl-camptothecin compound of the formula (5'):

(5')

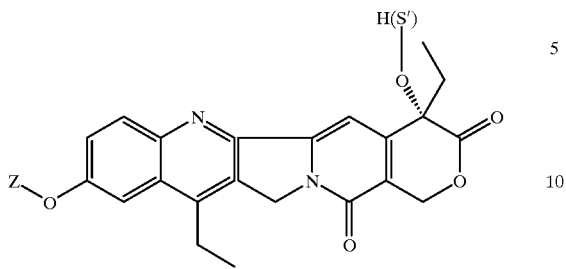

wherein the group (S') is a peptidyl spacer, and Z is as defined in claim 1, or a salt thereof.

9. A process for preparing a compound of the formula (5') as defined in claim 8, which comprises condensing a camptothecin compound of the formula (1) as defined in claim 6, with an N-protected-peptidyl compound of the formula (7):

wherein (S') is as defined in claim 8, $R_3$, represents an amino-protecting group, and P is a residue of an activated ester, to form a compound represented by the formula (8):

(8)

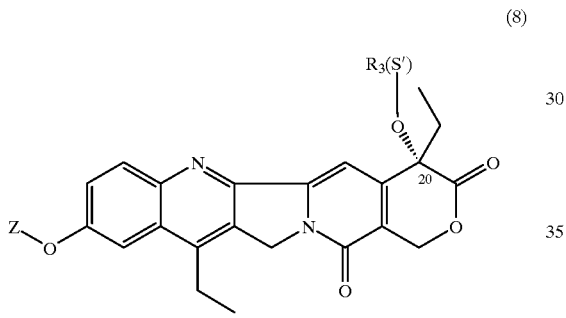

wherein Z'0 is $R_3(S')$ or $R_1CO$, and $R_1$, $R_3$ and (S') are as defined above, and then deblocking the N-protecting group of the substituent at position C-20 from the resulting compound.

10. A pharmaceutical composition, comprising a pharmaceutically acceptable carrier and, as active ingredient, the polymeric conjugate as defined in claim 1, or the compound of the formula (5') as defined in claim 8.

11. A process for preparing the compound of formula (5') as defined in claim 1, comprising:

(A) condensing a camptothecin compound of the formula (1):

(1)

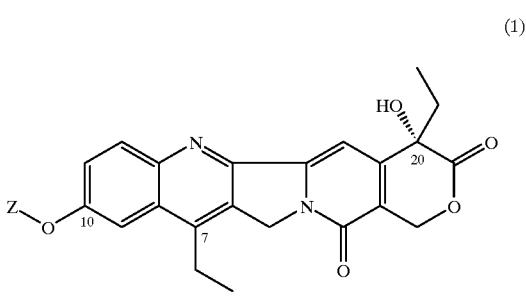

wherein Z is as defined in claim 1, with an N-protected-peptidyl compound of the formula (7):

wherein:
(S') is as defined in claim 1,
P is a residue of an activated ester,
to form a compound represented by the formula (8):

(8)

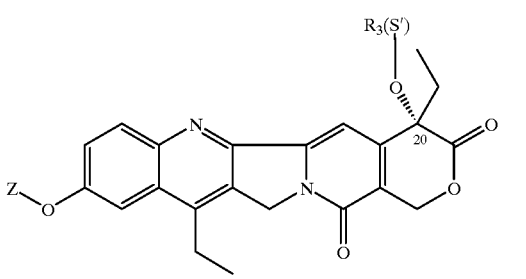

wherein Z' is $R_3(S')$ or $R_1CO$, and $R_1$, $R_3$ and (S') are as defined above, and then (B) deblocking the N-protecting group of the substituent at position C-20 from the resulting compound.

12. A pharmaceutical composition, comprising a pharmaceutically acceptable carrier, and a compound of the formula (5') as defined in claim 1.

* * * * *

UNITED STATES PATENT AND TRADEMARK OFFICE
CERTIFICATE OF CORRECTION

PATENT NO. : 6,376,617 B1 Page 1 of 1
DATED : April 23, 2002
INVENTOR(S) : Angelucci et al.

It is certified that error appears in the above-identified patent and that said Letters Patent is hereby corrected as shown below:

<u>Title page,</u>
Item [45] and the Notice information should read as follows:

-- [45] **Date of Patent: *Apr. 23, 2002**

[*] Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days. --

Signed and Sealed this

Tenth Day of September, 2002

Attest:

Attesting Officer

JAMES E. ROGAN
*Director of the United States Patent and Trademark Office*

UNITED STATES PATENT AND TRADEMARK OFFICE
CERTIFICATE OF CORRECTION

PATENT NO.    : 6,376,617 B1                                                   Page 1 of 1
DATED         : April 23, 2002
INVENTOR(S)   : Angelucci et al.

It is certified that error appears in the above-identified patent and that said Letters Patent is hereby corrected as shown below:

Column 6,
Line 12, "Washed with ethylene chloride" should read -- washed with methylene chloride --.
Line 46, "Campound A1" should read -- Compound A1 --.

Column 7,
Line 3, "N-(3-hydroxypropyl)" should read -- N-(2-hydroxypropyl) --.

Signed and Sealed this

Eighteenth Day of February, 2003

JAMES E. ROGAN
*Director of the United States Patent and Trademark Office*